(12) United States Patent
Jennissen et al.

(10) Patent No.: US 8,900,633 B2
(45) Date of Patent: Dec. 2, 2014

(54) METHOD FOR PRODUCING A PRODUCT HAVING A POLYMER MATRIX, IMPLANTS MADE THEREOF AND USE THEREOF

(75) Inventors: Herbert Jennissen, Cologne (DE); Maria Chatzinikolaidou, Heraklio-Kreta (GR)

(73) Assignee: Herbert Jennissen, Cologne (DE)

( * ) Notice: Subject to any disclaimer, the term of this patent is extended or adjusted under 35 U.S.C. 154(b) by 728 days.

(21) Appl. No.: 12/520,527

(22) PCT Filed: Dec. 19, 2007

(86) PCT No.: PCT/EP2007/064263
§ 371 (c)(1),
(2), (4) Date: Dec. 17, 2009

(87) PCT Pub. No.: WO2008/074845
PCT Pub. Date: Jun. 26, 2008

(65) Prior Publication Data
US 2010/0092558 A1    Apr. 15, 2010

(30) Foreign Application Priority Data

Dec. 20, 2006 (DE) .................. 10 2006 060 958

(51) Int. Cl.
| | | |
|---|---|---|
| A61K 9/12 | (2006.01) | |
| A61K 38/18 | (2006.01) | |
| A61L 17/00 | (2006.01) | |
| A61L 31/06 | (2006.01) | |
| A61L 27/54 | (2006.01) | |
| A61L 31/14 | (2006.01) | |
| A61B 17/86 | (2006.01) | |
| A61L 31/16 | (2006.01) | |
| A61L 27/34 | (2006.01) | |
| A61B 17/06 | (2006.01) | |

(52) U.S. Cl.
CPC .............. *A61L 31/148* (2013.01); *A61L 17/005* (2013.01); *A61L 2300/414* (2013.01); *A61L 31/06* (2013.01); *A61L 27/54* (2013.01); *A61B 17/06166* (2013.01); *A61B 17/06066* (2013.01); *A61B 17/866* (2013.01); *A61L 31/16* (2013.01); *A61L 27/34* (2013.01)
USPC .............. 424/484; 424/426; 514/8.8

(58) Field of Classification Search
None
See application file for complete search history.

(56) References Cited

U.S. PATENT DOCUMENTS

| | | | |
|---|---|---|---|
| 4,563,489 A | | 1/1986 | Urist |
| 5,385,887 A | * | 1/1995 | Yim et al. ................. 514/8.8 |
| 5,597,897 A | * | 1/1997 | Ron et al. ................. 530/350 |
| 5,741,329 A | * | 4/1998 | Agrawal et al. ............ 424/423 |
| 6,635,269 B1 | | 10/2003 | Jennissen |
| 7,211,275 B2 | | 5/2007 | Ying et al |
| 7,485,617 B1 | | 2/2009 | Pohl et al. |
| 2003/0161858 A1 | * | 8/2003 | Lidgren .................. 424/423 |
| 2004/0109937 A1 | * | 6/2004 | Jennissen et al. ............ 427/2.26 |
| 2005/0065214 A1 | | 3/2005 | Kronenthal |
| 2005/0084533 A1 | * | 4/2005 | Howdle et al. ............. 424/486 |
| 2006/0088565 A1 | | 4/2006 | Kohnert et al. |
| 2008/0069856 A1 | * | 3/2008 | Lyu et al. ................. 424/426 |
| 2008/0260799 A1 | | 10/2008 | Jennissen et al. |
| 2010/0028387 A1 | * | 2/2010 | Balasundaram et al. ...... 424/400 |
| 2010/0168854 A1 | | 7/2010 | Luers et al. |
| 2010/0255042 A1 | | 10/2010 | Jennissen et al. |

FOREIGN PATENT DOCUMENTS

| | | |
|---|---|---|
| AU | 2008320842 B2 | 5/2009 |
| EP | 1880739 A1 | 1/2008 |
| EP | 2 104 520 B1 | 3/2010 |
| WO | 9926674 A2 | 6/1996 |
| WO | 98/46289 A1 | 10/1998 |
| WO | 0209788 A1 | 2/2002 |
| WO | 03043673 A1 | 5/2003 |
| WO | 2004084965 A2 | 10/2004 |
| WO | 2004/105824 A1 | 12/2004 |
| WO | WO 2004/105824 A | 12/2004 |
| WO | WO 2005/065214 A1 | 3/2005 |
| WO | 2007053850 A2 | 5/2007 |
| WO | 2008098976 A2 | 8/2008 |

OTHER PUBLICATIONS

Sheridan et al. Bioabsorbable polymer scaffolds for tissue engineering capable of sustained growth factor delivery. J Control Release. Feb. 14, 2000;64(1-3):91-102.*

Yang et al. Human osteoprogenitor bone formation using encapsulated bone morphogenetic protein 2 in porous polymer scaffolds. Tissue Eng. Jul.-Aug. 2004;10(7-8):1037-45.*

Slurry, from Wikipedia, the free encyclopedia [online], [retrieved on Oct. 5, 2012]. Retrieved from the internet: URL<http://en.wikipedia.org/wiki/Slurry>.*

Kanczler et al.: "Supercritical carbon dioxide generated vascular endothelial growth factor encapsulated poly(dl-lactic acid) scaffolds induce angiogenesis in vitro," Biochemical and Biophysical Research Communications, Academic Press, Inc., Orlando, FL, US, vol. 352, No. 1, Nov. 30, 2006, pp. 135-141.

F.E. Wever et al.: "Slow and continuous application of human recombinant bone morphogenetic protein via biodegradable poly(lactide-co-glycolide) foamspheres," Int. J. Oral Maxillofac. Surg. 2002; 31:60-65.

M. H. Sheridan et al.: "Bioabsorbable polymer scaffolds for tissue engineering capable of sustained growth factor delivery," Journal of Controlled Release 64 (2000) pp. 91-102.

Lichtinger, T.K., et al, "Osseointegration of Titanium Implants by Addition of Recombinant Bone Morphogenetic Protein 2 (rhBMP-2)," Materialwiss. Werkstofftech, 2001, p. 937-941, vol. 32.

Spassova, E, et al., "Chemistry, Ultrastructure and Porosity of Monophasic and Biphasic Bone Forming Materials Derived from Marine Algae," Materialwiss. Werkstofftech, 2007, p. 1027-1034, vol. 38, No. 12.

Turhani, Dritan, et al., "Exogenous Recombinant Human BMP-2 Has Little Initial Effects on Human Osteoblastic Cells Cultured on Collagen Type I Coated/Noncoated Hydroxyapatite Ceramic Granules," Journal of Oral and Maxillofacial Surgery : Official Journal of the American Association of Oral and Maxillofacial Surgeons, Mar. 2007, p. 485-493, vol. 65, No. 3.

(Continued)

*Primary Examiner* — David Romeo
(74) *Attorney, Agent, or Firm* — Cahn & Samuels, LLP

(57) ABSTRACT

The invention concerns a method for the production of a product having a polymer matrix, products which can be produced in accordance therewith and the use thereof.

18 Claims, No Drawings

(56) References Cited

OTHER PUBLICATIONS

Zurlinden, K, et al., "Chemical Functionalization of a Hydroxyapatite Based Bone Replacement Material for the Immobilization of Proteins," Materialwissschaft und Werkstofftechnik, 2005, p. 820-827, vol. 36, No. 12.

Lange et al., "Critical Size Rib Defects in Sheep as a New Model for Testing rhBMP-2 Osteoinductivity of rhBMP-2/PDDLA". 8th World Biomaterials Congress, May 28-Jun. 1, 2008, Amsterdam, The Netherlands.

Lange et al., "rhBMP-2 Composite of Foamed Poly-(D,L-) Lactide as Drug Delivery System for Bone Tissue Engineering". 8th World Biomaterials Congress, May 28-Jun. 1, 2008, Amsterdam, The Netherlands.

Schliephake et al., "In vitro characterization of a slow release system of a polylactic acid and rhBMP2", Journal of Biomedical Materials Research Part A, p. 455-62, 2007.

Justesen, J. et al., "Maintenance of Osteoblastic and Adipocytic Differentiation Potential with Age and Osteoporosis in Human Marrow Stromal Cell Cultures," Calcified Tissue International, 2002, pp. 36-44, vol. 71.

Howdle, S., et al., "Supercrtical Fluid Mixing: Preparation of Thermally Sensitive Polymer Composites Containing Bioactive Materials," Chem. Commun., 2001, pp. 109-110, pp. 109-110.

McGee, J. Paul, et al., "Zero Order Release of Protein from Poly (D, L-lactide-co-glycolide) Microparticles Prepared using a Modified Phase Separation Technique," Journal of Controlled Release, 1995, pp. 77-86, vol. 34.

Valentin-Oprahn, A., et al., "Clincial Evaluation of Recombinant Human Bone Morphogenetic Protein-2," Clinical Orthopaedics and Related Research, 2002, pp. 110-120, No. 395.

Decision of European Opposition in EP 2 104 520 dated Nov. 20, 2012 and Partial English Translation thereof.

English Abstract of WO 9846289 dated Oct. 22, 1998.

English Abstract of WO 2008098976 dated Aug. 21, 2008.

English Abstract of WO 0209788 dated Feb. 7, 2002.

English Abstract of WO 9926674 dated Jun. 3, 1999.

Schliephake, H., et al., "Mandibular Bone Repair by Implantation of rhBMP-2 in a Slow Release Carrier of Polylactic Acid—An Experimental Study in Rats," Biomaterials, 2008, pp. 103-110, vol. 29.

Tschakaloff, A., et al., "Pilotstudie zur kontrollierten Freisetzung von Wachstumsfaktoren aus Polylaktidkoerpern," Mund Kiefer GesichtChir, 2000, pp. S474-S478, vol. 4.

Abstract of Eufinger, H., et al., "Interdisciplinary Design of Geometrically Structured Resorbable Implants of Cranioplastry—long-term in-vivo results in sheep", Essen, Germany, 2006.

Laub, M., et al., "Aspects of BMP-2 Binding to Receptors and Collagen: Influence of Cell Senescence on Receptor Binding and Absence of High-Affinity Stoichiometric Binding to Collagen", Mat-wiss. u. Werkstofftech, 2007, vol. 38, No. 12.

Johnson, M.D., E., et al., "Bone Morphogenetic Protein Augmentation Grafting of Resistant Femoral Nonunions: A Preliminary Report", Jun. 17, 1987.

Groeneveld, E H J, et al., "Bone Morphogenetic Proteins in Human Bone Regeneration", European Journal of Endocrinology, 2000, p. 9-21, vol. 142.

Pourtaheri, MD, S., et al., "Cervical Corpectomy with Ultra-Low-Dose rhBMP02 in High-Risk Patients: 5-Year Outcomes", Orthopedics, Dec. 2013, pp. 931-935, vol. 36, No. 12.

Valentin-Opran, MD, A., et al., "Clinical Evaluation of Recombinant Human Bone Morphogenetic Protein-2", Clinical Orthopedics and Related Research, 2002, pp. 110-120, No. 395.

Uludag, H., et al., "Delivery Systems for BMPs: Factors Contributing to Protein Retention at an Application Site", The Journal of Bone & Joint Surgery, 2001, vol. 83-A, supp. 1, part 2.

Long, S., et al., "Expression, Purification, and Renaturation of Bone Morphogenetic Protein-2 from *Escherichia coli*", Protein Expression and Purification, 2006, pp. 374-378, vol. 46.

Jennissen, H.P., et al., "Modificaiton of Metal Surfaces and Biocoating of Implants with Bone Morphogenetic Protein 2 (BMP-2)", DVM Bericht, 2000, pp. 127-140, vol. 313.

Lichtinger, T.K., et al., "Osseointegration of Titanium Implants by Addition of Recombinant Bone Morphogenetic Protein 2 (rhBMP-2)", Mat.-wiss. u. Werkstofftech, 2001, pp. 937-941, vol. 32.

Chatzinikolaidou, M., et al., "Peri-Implant Reactivity and Osteoinductive Potential of Immobilized rhBMP-2 on Titanium Carriers", Acta Biomaterialia, 2010, pp. 4405-4421, vol. 2010.

Ruppert, R., et al., "Human Bone Morphogenetic Protein 2 Contains a Heparin-Binding Site which Modifies its Biological Activity", Eur. J. Biochem., 1996, pp. 295-302, vol. 237.

Yamaguchi, A., et al., "Recombinant Human Bone Morphgenetic Protein-2 Stimulates Osteoblastic Maturation and Inhibits Myogenic Differentiation in Vitro", The Journal of Cell Biology, May 1991, pp. 681-687, vol. 113, No. 3.

Abstract of Schiller, C., "Polyester and Calciumphosphate als resorbierbare Biomaterialien," Dissertation, Ruhr-Universitaet Bochum, 2003.

Machine translation of Rasche, C., et al., "Beschickung abbaubarer Polymere mit thermolabilen Proteinen am Beispiel des Calmodulin", 2005.

* cited by examiner

METHOD FOR PRODUCING A PRODUCT HAVING A POLYMER MATRIX, IMPLANTS MADE THEREOF AND USE THEREOF

This application is a U.S. national stage application of PCT/EP2007/064263, which claims priority to application serial no. DE 10 2006 060 958.1.

The invention concerns a method of producing a product having a polymer matrix, products which can be obtained therefrom and use thereof.

The introduction of biologically active proteins such as for example growth factors into synthetic implantable polymers with subsequent liberation in the tissue while maintaining biological activity is a problem as yet unsolved in terms of biomaterial and implant research. A highly promising polymer which presents itself for resolving the problems is biodegradable polylactide. Thus attempts have already been made at an early time to introduce growth factors, inter alia BMP-2, into polylactides. Thus for example Weber et al. [(2002) Slow and continuous application of human recombinant bone morphogenetic protein via biodegradable poly(lactide-co-glycolide) foamspheres. *Int. J. Oral Maxillofac. Surg.*, 31, 60-65] were able to encapsulate rhBMP-2 in an amount of 170 µg/g of poly(lactide-co-glycolide) (PLGA) into the PLGA under drastic conditions (dichloromethane, 6M. urea), but almost complete liberation of the encapsulated rhBMP-2 already occurred within about 10 days.

Poly(D,L-lactide) is an amorphous polyester of D- and L-lactic acid with a glass transition temperature of about 57° C. By virtue of the absence of crystallinity, PDLLA is of lower strength and has a lower modulus of elasticity than crystalline poly(L-lactide) (PLLA). Particular advantages of the tissue-substitute material polylactide are strength over a number of weeks, degradability and the occurrence of the physiological monomer lactic acid as a final degradation product.

PLLA degradation in vitro and in vivo occurs in five phases:
  phase 1: hydratation;
  phase 2: depolymerisation without loss of mass (10-20 weeks, new bone trabeculae);
  phase 3: loss of mass;
  phase 4: absorption (2-5 years, absorption of fragments by phagocytes);
  phase 5: elimination (lactate is converted into pyruvate and metabolised).

For foaming polylactides, in the state of the art it is known from Sheridan, M. H., Shea, L. D., Peters, M. C., & Mooney, D. J. (2000) *J. Control Release*, 64, 91-102 that dry powders of polylactide-co-glycolide and lyophilised vascular endothelial growth factor VEGF are mixed and foamed up (59 bars), with the foam fragmenting. In other experiments, an open-pore structure was produced by foaming with NaCl. The liberation rates fluctuated between 2 and 70 days.

It was now found on the part of the inventors that stable products and in particular foams with bound-in bone growth factor can be produced from a mixture comprising a polylactide with a solution of at least one bone growth factor of the BMP class, in particular BMP-2.

The invention therefore concerns a method of producing a product having a polymer matrix, which includes the following steps:
  a) mixing a biodegradable polymer in powder form with an aqueous solution of a growth factor, cytostatic agent, antibiotic or mixtures thereof to form a slurry in such an amount that the aqueous solution is almost completely absorbed by the polymer in powder form;
  b) drying the slurry obtained in step a);
  c) introducing the product from step b) into a shaping apparatus; and
  d) shaping the product introduced into the shaping apparatus into an application form for promoting cell growth.

In that respect the inventors established as one of the essential elements of the invention that a slurry is formed, that is to say there is no supernatant liquid excess besides the powder. The primary "drying" of the slurry is in that case interpreted more as becoming spontaneously dry by virtue of the hygroscopy of the polymer powder like PDLLA powder. Hygroscopy provides that the aqueous solution with the for example BMP is sucked up into the polymer particles and presumably binds very finely and in adsorptive relationship to the polymer particles. In that respect generally 1.0 to 3.5 ml of the aqueous solution is used in relation to a gram of polymer and the polymer in powder form almost completely absorbs the aqueous solution so that a somewhat moist powder remains. As a secondary consideration a drying procedure, for example air drying or freeze drying with subsequent lyophilisation is used.

To maintain the growth factor, cytostatic agent, antibiotic or mixtures thereof in the drying operation in terms of biological activity and to protect them a polyvalent sugar such as sucrose can be present in the aqueous solution.

The absence of the supernatant liquid or a liquid phase in the slurry provides that only very small amounts of BMP not absorbed in the PDLLA powder remain between the PDLLA particles in the drying procedure. The greater the amount of liquid phase, that is to say particle-free phase, that is present, the correspondingly more "ice lumps" occur in the freeze-drying operation prior to lyophilisation. When those ice lumps dry extra-particular BMP-2 powder occurs. The inventors assume that it is this extra-particular BMP which is later not foamed up in that way that remains externally on the tablets and gives rise to the "burst phase" which is not the aim on the part of the inventors.

By means of the method according to the invention it is now possible to produce a resorbable osteoinductive polymer material for improved or accelerated bone healing and regeneration by liberation of the growth factor with simultaneous degradation of an individual pre-operatively produced implant. That can be achieved in particular by homogenous distribution of the growth factor, in particular BMP-2, with a high degree of possible loading with long-term liberation while maintaining biological activity.

The method according to the invention preferably uses a biodegradable polymer in powder form of a particle size of up to 500 µm. That biodegradable polymer is preferably polylactic acid, polyglycolic acid or copolymers thereof.

To stabilise the physiological medium upon degradation of the polymer in the body the biodegradable polymer in powder form can additionally include a pH-stabilisation agent such as $CaCO_3$, $NaHCO_3$, etc. A disadvantage of the polyacid such as polylactide is however the reduction in pH by a plurality of pH units during the hydrolysis operation, for which reason buffer substances (for example $CaCO_3$ or 80% $Na_2HPO_4$/20% $NaH_2PO_4$) can also advantageously be added to the polymer.

In a further embodiment 1.5 to 2.5 milliliters of the aqueous solution of the bone growth factor is used for one gram of the polymer.

That aqueous solution of the bone growth factor of the BMP class, in particular BMP-2, should involve a concentration of growth factor which permits from 0.5 mg to 10 mg of bone growth factor per gram of biodegradable polymers in the product. A particularly high level of loading of the polymer with bone growth factor can be achieved with an aqueous solution of the bone growth factor in the BMP class with a pH-value of 4 to 5, or with a pH-value of 9.5 to 10.5.

If the mixture of the polymer and the aqueous solution of the bone growth factor is not sufficiently capable of trickle flow the product obtained, the slurry, can be lyophilised for improved further processing.

In a next method step the lyophilisate can be introduced into an extruder as the shaping apparatus and can be extruded to form a granular material by means of the extruder at a temperature above the glass transition temperature of the biodegradable polymer and below the denaturing temperature of the bone growth factor. That gives a granular material which has a distribution of the growth factor in the polymer, that is already well homogenous.

A still more homogenous distribution can be achieved if the lyophilisate is introduced into an autoclave as the shaping apparatus, and subjected to pressure gassing with super-critical carbon dioxide in the autoclave above the glass transition temperature of the biodegradable polymer and below the decomposition temperature of the bone growth factor, then the autoclave is relieved of pressure and the resulting product in foam form is removed from the autoclave.

The product in foam form which is obtained in that way and which can also be further shaped to put it into the desired application form is distinguished by long-term liberation while maintaining biological activity, which is not known in the state of the art.

The desired application form includes as above a surgical fixing means such as thread, pin, nail, screw or rivets, a plate or a membrane, or use as coating means for metallic or ceramic implants, to which the product in foam form can be fused.

The invention therefore also concerns a product having a polymer matrix, obtained by the method according to the invention, as well as application forms produced therefrom such as a surgical fixing means such as thread, pin, nail, screw or rivets, a plate or a membrane, and use for producing a coating on implants and the implants coated in that way.

EXAMPLE OF PRODUCTION

In accordance with the invention, as an embodiment by way of example, the polylactide-calcium carbonate-composite (pH-stabilisation) comprising 2 g of poly(D,L-lactide) (200-500 µm of PDLLA, Resomer R 207 or R 208, Boehringer Ingelheim) is dissolved in 100 ml of chloroform, dispersed with $CaCO_3$ (Merck, p.a.) in the ratio (w:w=80:20) as prescribed, precipitated in 300 ml of ethanol, dried and mechanically ground to give a powder of a grain size of 200-400 µm (=PDLLA-$CaCO_3$ granular material).

Production of the PDLLA-$CaCO_3$-BMP-2 composite can then be effected as follows: 1 g of PDLLA-$CaCO_3$ granular material is absorbed in 1.6 ml of BMP-2 solution (125 µg/ml in unbuffered 15 mM sucrose, wherein the BMP-2 concentration can be up to 2 mg/ml in unbuffered 15 mM sucrose or in 15 mM sucrose buffered at pH 4.5 or pH 10.0) and homogenised in a Potter homogeniser with a Teflon pestle manually with rotary movements. During the homogenisation procedure the material was dried again so that once again there was a powder at the end of the homogenisation procedure. That powder was subjected to further processing either directly or after lyophilisation to give foamed tablets in a gassing method. In that respect the PDLLA-$CaCO_3$-BMP-2 powder mixture is subjected in a Teflon hollow mould (10×5×2 mm openings) to pressure gassing with supercritical $CO_2$ (100 bars) in an autoclave at a temperature of about 35-55° C. The glass transition temperature of the PDLLA, at a pressure of 100 bars, is <–50° C., that is to say at 100° C. above the glass transition temperature the polylactide is thermoplastic/fluid and dissolves the BMP-2. The PDLLA-$CaCO_3$-BMP-2 powder mixture is maintained under those conditions for about 2 hours (holding time). Then, within 20 minutes, the temperature is reduced to room temperature and the pressure to ambient pressure (decompression). Under those conditions a certain "porosity" is obtained, which can be increased by faster decompression. Under those conditions therefore the BMP-2 must withstand a pressure of 100 bars and a temperature of 55° C. to remain biologically active.

For the first time use was made on the part of the inventors of $^{125}$I-marked rhBMP-2 in order to be able to exactly trace the individual steps involved in production and the properties of foamed BMP-2-loaded polylactide tablets. It was possible to show that for example the bone growth factor rhBMP-2 can be incorporated in amounts of up to 3.4 mg/g of polylactide and that that rhBMP-2 is liberated at a speed constant of $1.6 \times 10^{-3}$ [d], that is to say with a half-life time of ~400 days. In that respect the liberated rhBMP-2 is active both in vitro and also in vivo.

Activity Measurements

Recombinant human "bone morphogenetic protein" (rhBMP-2) was produced by the inventors in *E. coli* in accordance with methods described hitherto with a degree of purity of >95%. The biological activity of the rhBMP-2 obtained in that way can be determined by means of a cell culture (MC3T3-E1 cells).

Radioactive marking of rhBMP-2 was effected in accordance with the chloramine-T method ($^{125}$I-rhBMP-2), as was described in the state of the art for the protein ubiquitin. The biological activity of the $^{125}$I-rhBMP-2 is fully retained with that method.

The loading of the biodegradable polymer could be demonstrated as mentioned above on the basis of PDLLA. PDLLA (poly(D,L-lactide) Resomer 207 and Resomer 208 (with a slightly different degree of polymerisation) was commercially obtained and dissolved in chloroform. A pH-stabilisation agent such as $CaCO_3$ can be added for pH-stabilisation during hydrolysis in the organism. The PDLLA/$CaCO_3$ mixture can be precipitated with an organic solvent such as ethanol, then dried, ground to give a fine powder and sieved (grain size ~200 µm) and mixed with a growth factor like rhBMP-2 in an aqueous solution. The resulting composite material is then foamed in an autoclave with supercritical $CO_2$ using the method of Tschakaloff et al. to give rectangular tablets (10×5×2 mm, ~35 mg/tablet).

For animal experiments, round tablets of a diameter of 5 mm and a height of 2 mm were used (~20 mg/tablet). The respective loading and the loading yield were determined by means of the $^{125}$I-rhBMP-2 (see above). The density of the foamed tablets was about 0.5 g/cm³.

Liberation of rhBMP-2

To measure the liberation kinetics, foamed tablets containing $^{125}$I-rhBMP-2 were placed in 1.5 ml of PBS buffer (phosphate buffered saline: 137 mM NaCl, 8.1 mM $Na_2HPO_4$, 2.7 mM KCl, and 1.5 mM $KH_2PO_4$, pH 7.4) in small reagent tubes and incubated with multiple changing with 1.5 ml of PBS for thorough mixing on a rotating wheel at room temperature for 107 days. At given times (buffer change) the tablets were removed from the reagent tubes, washed twice in fresh PBS (1.5 ml), transferred into new Eppendorf vessels with fresh PBS buffer and then measured in a gamma meter (Wizard™ 3, Wallac, Finland). The calculated half-life times were corrected in accordance with the spontaneous decomposition of the $^{125}$I ($t_{1/2}$=60 d).

Biological Activity Measurements

The biological activity of the soluble rhBMP-2 was measured by recording the dose action curve (induction of alkaline phosphatase) with MC3T3-E1 cells. Biological activity is specified as a half-activation constant ($K^r_{0.5}$), wherein the standard values for the constant are at 3-20 nM both for the rhBMP-2 produced by the inventor and also for the commercially available rhBMP-2 (InductOs, Wyeth).

Animal Experiments

Tablets containing rhBMP-2 (0.8-3.4 mg/g of PDLLA, Resomer 207) (5 mm in diameter×2 mm in height) were used in a critical defect healing model (sheep's rib) in 5 mm diameter bores, while observing animal protection regulations.

Preparation Production

The tissue samples were carefully freed of the soft part sheath immediately after being taken and introduced into phosphate-buffered formaldehyde solution (4.5%) for primary fixing. In accordance with a modified histological procedure for the production of undecalcified micro-section preparations in accordance with Prof. Donath the tissue samples after primary fixing were dehydrated in a rising alcohol series. To obtain the PDLLA components the samples were then embedded in Technovit 7200 VLC. After photopolymerisation of the embedding material 2 micro-sections of a thickness of 20 μm were produced from each sample. For surface colouring of the ground preparations when processing was finished, a 1% thionin solution was used.

Histomorphometry

Histomorphometric evaluation was effected by means of a semi-automatic image analysis program (Lucia, 32 g/4.51, Laboratory Imaging Ltd., Prague, Czech Republic) coupled to a transillumination microscope (Eclipse 800, Nikon Corp., Tokyo, Japan) with a 4-fold original magnification. For that purpose standardised measurement frames were positioned centrally over the defect region with the PDLLA tablets contained therein and the surface proportions for freshly formed bone tissue (mineralised and unmineralised) and empty space were ascertained and the proportion of PDLLA remaining was calculated from those values.

Structure of an Isotope Method for Measurement of the Loading

In order to be able to quantify the introduction of rhBMP-2 into PDLLA or also PLGA tablets as clearly, error-free as possible and with the highest level of sensitivity, the isotope method of radioiodination of rhBMP-2 to $^{125}$I-rhBMP-2 was adopted.

As described hereinbefore the PDLLA powder was mixed with rhBMP-2 and then foamed in the high-pressure gassing installation. The results are set forth in the following Table.

TABLE 1

Loading of PDLLA tablets with $^{125}$I-rhBMP-2[1]

| Weight of $^{125}$I-rhBMP-2 in the batch [mg/g] | Loading found with $^{125}$I-rhBMP-2 [mg/g] |
|---|---|
| 0.3 | 0.342 ± 0.032 (10) |
| 0.5 | 0.475 ± 0.047 (10) |
| 1.0 | 1.0 ± 0.145 (10) |

[1] The table specifies mean value and standard deviation, n in brackets (see also: Lange, M., Sänger, T., Chatzinikolaidou, M., Laub, M., Jennissen, H. P. (2008) "rhBMP-2 composite of foamed Poly-(D,L-) lactide as drug delivery system for bone tissue engineering" Abstract Commun. 8th World Congress on Biomaterials, May 28-Jun. 1, 2008, Amsterdam, NL).

As can be seen from Table 1 loading levels of 0.34-1.0 mg of $^{125}$I-rhBMP-2 per g of tablet could be obtained, with good yields. The tests show that an effective method of loading the tablets was developed here.

Liberation Tests

The tablets produced as in Table 1 could be used at the same time for the liberation tests by virtue of the radioactive marking of the rhBMP-2. As the inventor noted incubation of $^{125}$I-rhBMP-2/PDLLA tablets in PBS buffer of pH 7.4 led to slow liberation of the $^{125}$I-rhBMP-2 over a period of 107 days. Non-linear adaptation to a two-phase exponential function led to good adaptation so that the speed constants and the half-life times could be easily ascertained. For the progress in terms of time there was liberation in two phases, an initial so-called burst phase within the first 1-3 days with a half-life time of $t_{1/2}$~0.3-0.5 d and a second slow prolonged monoexponential main phase for the rest of the observation time with a half-life time of $t_{1/2}$~400-469 d. The long half-life times of the second and thus main phase give rise to the conclusion that there are no pores for liberation of the $^{125}$I-rhBMP-2 in the foamed PDLLA, but that liberation begins only with hydrolysis or decomposition of the PDLLA. Accordingly binding of the $^{125}$I-rhBMP-2 at the surface of the tablet in relatively large amounts, except in the case of the burst phase, is also improbable. A summary of the kinetic and statistical data is to be found in the following Table. The speed constants for liberation of the $^{125}$I-rhBMP-2 of the three differently loaded PDLLA tablets are between $k^b_{-1}$=1.5-1.7× $10^{-3}$ [$d^{-1}$] or ($k^b_{-1}$~2.0×$10^{-8}$ [$s^{-1}$]).

TABLE 2

| rhBMP-2 loading | Half-life time of rhBMP-2 [d] | | Speed constants of liberation | | |
|---|---|---|---|---|---|
| [mg/g] | $t_{1/2}$ 1 | $t_{1/2}$ 2 | $k^a_{-1}$ [$d^{-1}$] | $k^b_{-1}$ [$d^{-1}$] | [$r^2$] |
| 0.342 ± 0.032 | 0.48 | 404.2 | 1.45 ± 0.53 | 0.00172 ± 0.000154 | 0.966 |
| 0.475 ± 0.047 | 0.27 | 440.4 | 2.59 ± 0.80 | 0.00157 ± 0.000122 | 0.972 |
| 1.0 ± 0.145 | 0.41 | 469.0 | 1.71 ± 0.54 | 0.00148 ± 0.000123 | 0.971 |

2) The Table specifies mean values and standard errors, n = 20. The half-life times are corrected in accordance with the spontaneous decomposition of $^{125}$I ($t_{1/2}$ = 60 d). The calcite-bearing tablets weighed 35 mg.
1) Specified are mean value and standard deviation, n in brackets (see also: Lange, M., Sänger, T., Chatzinikolaidou, M., Laub, M., Jennissen, H. P. (2008) "rhBMP-2 composite of foamed Poly-(D,L) lactide as drug delivery system for bone tissue engineering" Abstract Commun. 8th World Congress on Biomaterials, May 28-Jun. 1, 2008, Amsterdam, NL).

As shown in Table 3 hereinafter the absolute amounts of liberated $^{125}$I-rhBMP-2 (initial loading, 1.0±0.145 mg/g) were calculated for various periods of time. In 107 days a total of 230 μg of $^{125}$I-rhBMP-2/g of PDLLA, that is to say (23% of the total amount) was liberated. In the burst phase, it was 93 μg/g within one day. As shown in Table 3 hereinafter therefore a three-month, constant and highly effective stimulation of bone growth is possible.

TABLE 3

Liberated absolute amounts of $^{125}$I-rhBMP-2 from 10 tablets loaded with 1.0 mg/g over a period of 107 days[3]

| Period | $^{125}$I-rhBMP-2 liberation μg/day × g | $^{125}$I-rhBMP-2 total amount liberated μg/g |
|---|---|---|
| 1st day | 93 | 93 |
| 3rd-10th days | 5.6 | 132 |
| 10th-19th days | 1.2 | 142 |
| 19th-48th days | 1.7 | 192 |
| 58th-107th days | 0.8 | 230 |

[3] The liberated amounts of $^{125}$I-rhBMP-2 were calculated on the basis of the data in Table 2.

Interestingly, a constant liberation speed of 0.8-1.2 μg/day×g was obtained over a long period of 93 days. If the concentration of liberated rhBMP-2 from a 20 mg tablet (=20 ng/day) in a bone defect (∅=5 mm×2 mm depth) of the volume of ~40 µl is calculated for an average liberation rate of 1.0 µg/day×g that gives the value ~20 nM, which signifies almost maximum stimulation of the MC3T3-T3 cells in vitro.

The tablets obtained in accordance with the invention (10× 5×2 mm) weighed 40-60 mg/tablet and contained 20-80 µg of BMP-2/tablet. The structure of the foamed PDLLA is sponge matrix-like and the biological activity of the bone growth factor is maintained almost unchanged.

Indication of the Biological Activity of rhBMP-2/PDLLA Tablets in Animal Tests

As mentioned hereinbefore animal testing was carried out on the part of the inventors using a sheep's rib. Formed in the ribs were hole defects (∅=5 mm×2 mm in depth) into which PDLLA tablets of the same size (20 mg), loaded with BMP-2, were introduced in accurately fitting relationship. After 8 weeks rest period the sheep were slaughtered and the ribs removed. Histomorphometric evaluation of the ground section preparations dyed with thionin solution was effected by means of a semi-automatic image analysis program (Lucia 32 g/4.51, Laboratory Imaging Ltd.) coupled to a transillumination microscope (Eclipse 800, Nikon), with a 4-fold original magnification. The surface proportions were determined for regenerated bone tissue (mineralised and unmineralised) and the empty space was determined. As a marked difference, it is possible to see on the empty preparations (without rhBMP-2) only scanty point areas with bone regeneration and they are preferably at the periphery of the preparations at the transition to the local bone of the defects or in immediately subperiostal relationship. In contrast thereto bone regeneration is seen to be markedly more extensive in the rhBMP-2 preparations. The multiple areas with bone regeneration are also diffusely distributed over the entire cross-section of the PDLLA tablets and are not just peripherally grouped. A significantly more strongly pronounced bone regeneration also entails increased breakdown of the PDLLA material with markedly more numerous resorption locations.

A quantitative evaluation of the animal tests is summarised in Table 4. Two kinds of control were implemented: control 1 in a rib where only implants without rhBMP-2 were used and control 2 in which BMP-2-bearing implants were present in the same rib. As can be seen from Table 4 the controls 2 are always above the controls 1, which means that the rhBMP-2, in neighbouring relationship with the controls 2, already leads to a marked increase in bone growth in the preparations. The controls 2 were therefore not acknowledged by the inventors as genuine controls. If now the rhBMP-2-bearing tablets (0.8-3.4 mg/g) are compared to the control 1, it is found that there is a significant increase in the percentage proportion of the regenerated bone (p<0.05, in the non-paired, two-sided t-test). With a content of 3.4 mg/g the proportion of regenerated bone was even significantly greater than the control 2. The incorporation of rhBMP-2 in foamed-up PDLLA tablets therefore leads to strong stimulation of bone growth and replacement of the PDLLA by bone in the rib model of the sheep after 8 weeks.

TABLE 4

De novo bone formation (morphometry) in a "critical size defect" in sheep ribs 8 weeks after implantation

| Resomer 207 | Bone, % | $\bar{x} \pm s$ % | P (against control 1) | P (against control 2) |
|---|---|---|---|---|
| Control 1 | 0.81 | 1.34 ± 0.86 | — | — |
|  | 0.87 |  |  |  |
|  | 2.34 |  |  |  |
| Control 2 | 4.40 | 2.93 ± 1.48 | — | — |
|  | 2.95 |  |  |  |
|  | 1.43 |  |  |  |
| 0.8 mg/g rhBMP-2 | 5.22 | 7.79 ± 7.50 | 0.2129 | 0.3321 |
|  | 16.25 |  |  |  |
|  | 1.92 |  |  |  |
| 18 mg/g rhBMP-2 | 5.44 | 5.22 ± 2.12 | 0.0426 | 0.1995 |
|  | 3.00 |  |  |  |
|  | 7.22 |  |  |  |
| 3.4 mg/g rhBMP-2 | 7.58 | 8.18 ± 2.69 | 0.0137 | 0.0413 |
|  | 11.12 |  |  |  |
|  | 5.85 |  |  |  |

[3] Specified are mean values and standard deviations, n = 3. Significance is given at P < 0.05. This involves tablets of a diameter of 5 mm and a thickness of 2 mm. The weight was 20 mg (see also: Lange, M., Spassova, E., Laub, M., Schopper, C., Sänger, T., Stoev, V., Ewers, R., Jennissen, H. P. (2008) "Critical Size Rib Defects in Sheep as a New Model for Testing rhBMP-2 osteoinductivity of rhBMP-2/PDLLA" Abstract Commun. 8th World Congress on Biomaterials, May 28-June 1, 2008, Amsterdam, NL).

On the basis of the measurement results it is confirmed that the polylactide composite according to the invention is a material which contains a polylactide matrix (mechanically stable implant or place holder, bone substitute material), $CaCO_3$ for buffering the lactic acid occurring upon hydrolysis and BMP-2 for osteoinduction, which can be used outstandingly for enhancing bone growth.

The matrix according to the invention with bone growth factor can in that respect be advantageously used in the following forms:
  pins, nails, screws
  plates, membranes
  coating on metal implants
which can also be enhanced in their effectiveness by means of local thermal treatment at the location of application, in the patient. In all cases with or without local thermal treatment at the location of application, by way of example, BMP-2 withstands temperatures without denaturing at up to 100° C.

The shaped bodies produced in that way can thus be fused to the tissue by means of a sonic welding process upon implantation into the tissue.

The invention claimed is:

1. A method of producing a product having a polymer matrix comprising the steps of:
   a) mixing a biodegradable polymer in powder form with an aqueous solution of a bone growth factor of the bone morphogenetic protein (BMP) class to form a slurry in such an amount that the aqueous solution is almost completely absorbed by the polymer in powder form,
   wherein the slurry comprises no supernatant liquid;
   wherein the biodegradable polymer has a particle size of less than or equal to 500 µm, and is selected from the group consisting of polylactic acid, polyglycolic acid, and copolymers thereof;
   wherein the aqueous solution has a concentration of 0.5 mg to 10 mg of bone growth factor per gram of biodegradable polymer in the product and wherein the pH-value of the aqueous solution is 4 to 5 or 9.5 to 10.5;
   b) drying the slurry obtained in step a);
   c) introducing the product from step b) into a shaping apparatus; and d) shaping the product introduced into the shaping apparatus into an application form for promoting cell growth, wherein the dried slurry is introduced into an autoclave as the shaping apparatus, subjected in the autoclave to pressure gassing with supercritical carbon dioxide above the glass transition temperature of the biodegradable polymer and below the decomposition temperature of the bone growth factor, and removed from the pressure-relieved autoclave as a product in foam form.

2. The method according to claim 1, wherein a cytostatic agent, an antibiotic or a mixture thereof is additionally used in step a).

3. The method according to claim 1, wherein the bone growth factor is BMP-2.

4. The method according to claim 1, wherein the biodegradable polymer in powder form additionally contains a pH-stabilisation agent.

5. The method according to claim 1, wherein 1 to 3.5 milliliters of the aqueous solution is used for one gram of the polymer.

6. The method according to claim 1, wherein the slurry produced in step a) is lyophilised.

7. The method according to claim 2, wherein the bone growth factor is BMP-2.

8. The method according to claim 2, wherein the biodegradable polymer in powder form additionally contains a pH-stabilisation agent.

9. The method according to claim 2, wherein 1 to 3.5 milliliters of the aqueous solution is used for one gram of the polymer.

10. The method according to claim 5, wherein 1.5 to 2.5 milliliters of the aqueous solution is used for one gram of the polymer.

11. The method according to claim 9, wherein 1.5 to 2.5 milliliters of the aqueous solution is used for one gram of the polymer.

12. The method according to claim 1, wherein the bone growth factor comprises BMP-2 and the biodegradable polymer comprises poly(D,L-lactide) and a $CaCO_3$ pH-stabilization agent.

13. A method of producing a product having a polymer matrix, comprising:
mixing 1) a biodegradable polylactic polymer in powder form having a particle size of less than or equal to 500 μm, and a pH-stabilization agent with 2) an aqueous solution comprising a bone growth factor of the bone morphogenetic protein class to form a slurry in which the aqueous solution is almost completely absorbed by the polylactic polymer, thereby forming a moist powder, wherein 1 to 3.5 milliliters of aqueous solution is used for 1 gram of the biodegradable polylactic polymer, and wherein the pH-value of the aqueous solution is 4 to 5 or 9.5 to 10.5;
drying the slurry;
introducing the dried slurry into an autoclave and subjecting the dried slurry to a pressure of 100 bars of supercritical carbon dioxide at a temperature of about 35-55° C. for about 2 hours;
reducing the pressure to ambient pressure; and
removing product in foam form from the autoclave.

14. The method according to claim 13, wherein the biodegradable polymer has a particle size of 200 to 400 μm.

15. The method according to claim 13, wherein the product comprises 0.5 mg to 10 mg of bone growth factor per gram of biodegradable polymer.

16. The method according to claim 13, wherein the bone growth factor comprises BMP-2 and the biodegradable polymer comprises poly(D,L-lactide) and a $CaCO_3$ pH-stabilization agent.

17. The method according to claim 13, further comprising shaping the product into an application form, wherein the application form has an initial burst phase with a half-life of bone morphogenetic protein of about 0.3 to 0.5 days and a second liberation phase with a half-life of bone morphogenetic protein of about 400 to 469 days.

18. The method according to claim 13, wherein the slurry comprises no supernatant liquid.

\* \* \* \* \*